United States Patent
Xing et al.

(10) Patent No.: US 8,653,329 B2
(45) Date of Patent: Feb. 18, 2014

(54) CLONING AND APPLICATION OF A PLEIOTROPIC GENE GHD7 THAT CONTROLS GRAINS YIELD, HEADING DATE AND PLANT HEIGHT OF RICE

(75) Inventors: Yongzhong Xing, Wuhan (CN); Qifa Zhang, Wuhan (CN); Weiya Xue, Wuhan (CN)

(73) Assignee: Huazhong Agricultural University, Hubei Province (CN)

( * ) Notice: Subject to any disclaimer, the term of this patent is extended or adjusted under 35 U.S.C. 154(b) by 439 days.

(21) Appl. No.: 12/677,984

(22) PCT Filed: Sep. 10, 2008

(86) PCT No.: PCT/CN2008/001598
§ 371 (c)(1), (2), (4) Date: Oct. 6, 2011

(87) PCT Pub. No.: WO2009/033369
PCT Pub. Date: Mar. 19, 2009

(65) Prior Publication Data
US 2012/0023621 A1      Jan. 26, 2012

(30) Foreign Application Priority Data
Sep. 12, 2007 (CN) .......................... 2007 1 0053199

(51) Int. Cl.
*C12N 15/82* (2006.01)
*C12N 15/87* (2006.01)
*A01H 1/00* (2006.01)
*A01H 5/00* (2006.01)
*C12N 5/04* (2006.01)
*C12N 5/10* (2006.01)

(52) U.S. Cl.
USPC ............ 800/290; 800/298; 435/468; 435/419

(58) Field of Classification Search
USPC ........................................................ 800/290
See application file for complete search history.

(56) References Cited

U.S. PATENT DOCUMENTS

| 2004/0123343 A1 | 6/2004 | La Rosa et al. |
| 2006/0059586 A1* | 3/2006 | Cheng et al. .................. 800/287 |
| 2012/0017338 A1 | 1/2012 | Wu et al. |

FOREIGN PATENT DOCUMENTS

| CN | 101148674 | 3/2008 |
| WO | 0018963 | 4/2000 |
| WO | WO 2004/081210 | * 9/2004 |

OTHER PUBLICATIONS

Xue et al., Natural variation in Ghd7 is an important regulator of heading date and yield potential in rice, 40 Nature Genetics No. 6, 761-767 at 764 (2008).*

(Continued)

*Primary Examiner* — Cynthia Collins
*Assistant Examiner* — Rebecca Coobs
(74) *Attorney, Agent, or Firm* — Thompson Coburn LLP; Charles P. Romano

(57) ABSTRACT

The cloning and application of a pleiotropic gene Ghd7 that controls grains yield, heading date and plant height of rice are provided. The gene has the nucleotide sequence as shown in SEQ ID NO: 1. The sequence of the present gene is 3,917 bp in length, contains two exons and encodes 257 amino acids. The cDNA sequence of the gene is as shown in SEQ ID NO: 1. The present gene encodes a protein having the CCT domain of CO protein and having the amino acid sequence as shown in SEQ ID NO: 1. Rice plants transformed with GHD7 gene are obtained using transgenic technology. The transgenic plants all exhibit markedly increased yield, larger number of spikelets per panicle, delayed heading date and elevated plant height as compared to their respective controls (wild type receptors plants). The trait changes are quite consistent with the phenotypes of the two parent genotypes of GHD7 near isogenic lines of Zhenshan 97. The methods for gene cloning, breeding of near isogenic lines and transgene manipulation are also provided, as well as the application of pleiotropic gene GHD7 in research of rice breeding and plant evolution.

8 Claims, 6 Drawing Sheets

(56) References Cited

OTHER PUBLICATIONS

Robson et al., Functional importance of conserved domains in the flowering-time gene CONSTANS demonstrated by analysis of mutant alleles and transgenic plants, 28 Plant Journal No. 6, 619-631 at 626-627 (2001).*

Xue, Weiya et al., Natural variation in Ghd7 is an important regulator of heading date and yield potential in rice, Nature Genetics, May 4, 2008, pp. 761-767, vol. 40 No. 6.

GenBank Accession No. AEG78653, Ghd7 [Oryza sativa Japonica Group], first seen at NCBI Aug. 20, 2011.

GenBank Accession No. AEG78658, Ghd7 [Oryza sativa Japonica Group], first seen at NCBI Aug. 20, 2011.

GenBank Accession No. AEG78661, Ghd7 [Oryza sativa Japonica Group], first seen at NCBI Aug. 20, 2011 12:08 AM.

GenBank Accession No. AEG78662, Ghd7 [Oryza sativa Japonica Group], first seen at NCBI Aug. 20, 2011.

GenBank Accession No. AER41603, CCT+motif+family+protein [Oryza glaberrimal], first seen at NCBI on Nov. 5, 2011.

GenBank Accession No. AER41622, CCT+moti f +fami ly+protein [Oryza glumipatula], first seen at NCBI on Nov. 5, 2011.

Strayer, Carl et al., "Cloning of the Arabidopsis Clock Gene TOC1, an Autoregulatory Response Regulator Homolog" Science, Aug. 4, 2000, pp. 768-771, vol. 289.

* cited by examiner

```
  1 msmgpaages cglcgadggg ccsrhrhddd gfpfvfppsa cqgigapapp
 51 vhefqffgnd ggxddgesva wlfddyppps pvaaaagmhh rqppydgvva
101 ppslfrrnts agaltfdvsl ggrpdldagl glgggsgrha eaaasatims
151 ycgstftdaa ssmpkemvaa madvgeslnp ntvvgamver eaklmrykek
201 rkkrcvekql rvasrkayae mrprvrarfa keadqeavap pstyvdpsrl
251 elgqwfr
```

CLONING AND APPLICATION OF A PLEIOTROPIC GENE GHD7 THAT CONTROLS GRAINS YIELD, HEADING DATE AND PLANT HEIGHT OF RICE

CROSS-REFERENCE TO RELATED APPLICATIONS

This application is a National Stage application of International Patent Application No. PCT/CN2008/001598, filed Sep. 10, 2008 and incorporated by reference herein in its entirety, which claims priority to Chinese Patent Application CN 200710053199.4, filed Sep. 12, 2007 and incorporated by reference herein in its entirety.

TECHNICAL FIELD

The present invention relates to the field of plant genetic engineering. Particularly, the present invention relates to the cloning and use of a pleiotropic gene Ghd7 that controls grains yield, heading date and plant height of rice.

INCORPORATION OF SEQUENCE LISTING

An electronic form of the sequence listing is contained in the file named "38_21_56283_SEQLST_ST25.txt", which is 17584 bytes (as measured in MS-DOS) and comprises 32 sequences, is filed herewith and is herein incorporated by reference.

BACKGROUND OF THE INVENTION

Grain yield of rice is one of the most important ultimate traits in rice production. It is a composite trait of number of grains per panicle, number of effective ears and weight per thousand grains. The number of grains per panicle is dependent on number of spikelets per panicle and seed setting rate. Extensive research has shown that the number of spikelets per panicle determines rice yield to a great extent due to its relatively higher heritability and bigger contribution to yield and therefore much attention has been paid to this trait. Heading date is an important biological trait that directly determines the ecoadaptation and season adaptation of rice varieties. And plant height is closely related to biological yield and the harvest index and influences the stability of yield. Therefore, elucidation of the genetic basis and molecular mechanism of number of grains per panicle, heading date and plant height may facilitate the modification of high yield and yield stability of rice.

Heading date is under the regulation of basic nutritional genes and photoperiod-sensitivity genes (Tanisaka et al. Jpn J Breeding, 1997, 442: 657-668; Tsai, Rice genet Newslett, 1985, 2:77-78). The regional distribution of rice varieties and differentiation of indica rice and japonica rice are also believed to be associated with the evolution of heading date genes. Therefore, revelation of the genetic basis of heading date may lend clues to research on rice evolution and provide theoretical guidance on the breeding selection of rice varieties of different ecotypes. As demonstrated by both classical genetics means and molecular genetics means, heading date is controlled by several qualitative trait loci and many quantitative trait loci (QTLs). Among the QTLs, a heading date QTL in the C1023-R1440 region near the centromere of the rice chromosome 7 (this QTL was named as Ghd7 in the present invention) was detected in different rice populations such as population of the Indica-Japonica cross (Li et. al., 2003, Theor. Appl. Genet. 108: 141-153), population of the Indica-Indica cross (Xing et. al., 2002, Theor. Appl. Genet. 105:248-257), population of the Japonica-Japonica cross (Lin et. al., 2003, Breeding Sci. 53: 51-59) and wild-cultivated population (Thomson et. al., 2003, Theor. Appl. Genet. 107: 479-493), but its genetic effect differed greatly among different populations. Our laboratory, using Zhenshan 97/Minghui 63 derived $F_{2:3}$ and recombinant inbred line population, also detected a QTL controlling heading date in the Ghd7 region many times, which explained up to about 25% of total heading date variation (Xing et. al., 2001, Acta. Bot. Sin. 43:721-726; Yu et. al., 2002, Theor. Appl. Genet. 104: 619-625). These results showed that Ghd7 gene can be stably expressed under different genetic backgrounds and in different environments. Genetics research of many years suggest that plant height is also controlled by several qualitative trait loci and many QTLs. A QTL that influences plant height and is affected by the environment was also found present in the Ghd7 region in different populations (Li et. al., 1996, Genetics, 145: 453-465; Li et. al., 2003, Theor. Appl. Genet. 108: 141-153; Li et. al., 2006, The New Phyto. 170: 185-193; Xiao et. al., 1996, Theor Appl Genet, 92: 230-244). Also, a QTL that influences grain yield trait was detected in this region in some populations (Brondani et. al., 2002, Theor Appl Genet, 104: 1192-1203; Li et. al., 1996, Genetics). We cultivated the Zhenshan 97/Minghui 63 $F_2$, RIL and "Yongjiu $F_2$" populations in the same season of different years in the same location, and found that this QTL was capable of controlling heading date, plant height, number of spikelets per panicle and yield in the populations of different generations derived from the same combination (Yu et. al., 1997, Proc. Natl. Acad. Sci. USA 94:9226-9231; Xing et. al., 2001, Acta. Bot. Sin. 43:721-726; Yu et. al., 2002, Theor. Appl. Genet. 104:619-625; Xing et. al., 2002, Theor. Appl. Genet. 105: 248-257; Hua et. al., 2002, Genetics 162:1885-1895). This has not been reported by other research groups. Ghd7 influenced number of spikelets per panicle, heading date and plant height at the same time. The Minghui 63 allele increased the phenotype values of these three traits. Therefore, there is great potential and prospect for Ghd7 in the modification of rice yield and variety adaptation. Accurate mapping and cloning of Ghd7 may provide a novel gene resource for the high-yield breeding of rice.

It is almost impossible to accurately map the quantitative trait loci using primary mapping population, because in such a population many QTLs that influence the same trait are isolated. The interference among the QTLs and the influence of environmental factors greatly limit the accuracy of QTL mapping. In addition, for a QTL-rich region, it is very difficult to judge whether it is one pleiotropic QTL or many minor QTLs that play a role (Yano et. al., 1997, Plant Molecular Biology 35:145-153). Therefore, advanced mapping populations must be constructed in order to accurately map QTL. A common practice is construction of near isogenic lines of the target QTL to eliminate most of the background difference outside the target QTL site so that the site exhibits typical Mendelian inheritance, that is, conversion of quantitative traits to qualitative traits. This approach has played an important role in the accurate mapping and gene cloning research of many QTLs. Fan et. al. have mapped GS3 to a 7.9 kb region and conducted map-based cloning of GS3 using this approach (Fan et al., 2006, Theo Appl Genet. 112: 1164-1171). Due to the restriction of population size or the frequently-occurred recombination inhibition in the region near the centromere, sometimes the resolution of gene mapping is insufficient to locate the target gene, and this brings trouble to map-based cloning. So a candidate gene cloning approach is a relatively good strategy. All the genes in the mapping region are analyzed; based on the characteristics and relevant functions of the cloned gene domain and by comparison of the functions of known genes and profiles of predicted genes, structurally and functionally relevant genes are selected as the candidate genes for functional verification. This candidate gene strategy provided a new approach for the separation and cloning of Ghd7 gene.

A gene, Ghd7, that controls grain yield, heading date and plant height in rice was isolated and cloned through candidate gene cloning approach in the present invention, to provide a novel gene resource for breeding rice in terms of yield and variety and to lend clues to research on the evolution of crops.

SUMMARY OF THE INVENTION

An object of the present invention is to isolate and clone from rice a pleiotropic gene that concurrently controls grain yield, heading date and plant height in rice using candidate gene cloning approach, to overcome the shortcomings of prior art. The present invention also relates to the application of this gene in the breeding of rice to greatly increase rice yield. This gene was designated as Ghd7 by the present applicants.

The present invention was realized as follows. From the recombinant inbred line population derived from the combination of Zhenshan 97 (a publicly known and used rice variety) and Minghui 63 (a publicly known and used rice variety), applicants selected a plant comprising Ghd7 gene and having a genetic background 70% identical to that of Zhenshan 97. The selected plant was used to conduct backcrossing with Zhenshan 97 for two generations followed by inbreeding to construct Ghd7 near isogenic lines. Analysis of the population of near isogenic lines revealed that the gene had a great effect on heading date, number of spikelets per panicle and plant height (Table 2). A progeny test showed that the gene exhibited a Mendelian segregation ratio (Table 2). Using the large population of near isogenic lines, Ghd7 was accurately mapped to a chromosome region of 0.4 cM, about 2,300 kb (FIG. 3). Prediction of the genes in the region led to the discovery of a gene with CCT domain. Positive clones comprising Ghd7 were screened from the BAC library of Minghui 63, and were subcloned to obtain a 8,175 bp genomic fragment as the candidate gene for Ghd7 which was subjected to transgene verification. The gene was introduced into Mudanjiang 8 and Hejiang 19 (both are publicly known and used rice varieties) and the transgenic individual plants all exhibited marked increase in yield and number of spikelets per panicle, marked delay of heading date and higher plant height (as shown in Table 4). The full-length cDNA of Ghd7, 1,014 bp in length, was isolated using rapid-amplification of cDNA ends (RACE) method (Frohman et. al., 1988, Proc Natl. Acad Sci USA, 1988, 85: 8998-9002). Comparison of genome sequence and full-length cDNA sequence revealed that the Ghd7 gene comprises two exons and encodes a total of 257 amino acids. Gene expression analysis showed that the gene is expressed in all tissues with low expression level in all the growth stages. Test of the light cycle reaction showed that the expression amount of Ghd7 is elevated and heading is delayed under long-day condition as compared to short-day condition. The allele of Zhenshan 97 was absent. Four large ear varieties, i.e. Minghui 63, H94 (from Shanghai Agrobiological Gene Centre), 93-11 (a medium indica variety bred by the Agricultural Science Research Institute in Lixia River Area, Jiangsu Province) and Teqing (a high-yield rice variety widely extended in the 1980's), two small ear varieties, i.e. Mudanjiang 8 and Hejiang 19, and two varieties with intermediate ear size, i.e. Zhonghua 11 (a commercial variety from Crops Research Institute of The Chinese Academy of Agricultural Sciences) and Nipponbare (a publicly known and used rice variety whose whole genome sequencing has been completed) was sequenced and compared. Sequencing the alleles of these eight plants revealed that, in the 5.5 kb sequence region comprising the promoter and whole gene, the first exon in four large ear varieties had a common variation compared with two small ear varieties, i.e. GAG encoding glutamic acid is mutated to the stop codon (TGA).

The present invention has the following advantages:

1. The present invention cloned a pleiotropic gene that concurrently influences grain yield, heading date and plant height from rice for the first time. Therefore the present invention provides a new gene resource for the breeding of high-yield varieties and varieties able to adapt to different ecotypes and seasons, and also provides gene sequence for the cloning of relevant genes in other crops using a homologous gene method.

2. The gene cloned in the present invention may also provide evidence for research on the light reaction and molecular evolution of cereal crops such as rice (*Oryza sativa*) and dicotyledonous crops such as oil-seed rape (*Brassica napus*).

BRIEF DESCRIPTION OF THE DRAWINGS

SEQ ID NO: 1 in the Sequence Listing is Ghd7 genomic sequence isolated and cloned in the present invention (which includes the coding sequence of Ghd7 gene).

FIG. 2. The frequency distribution of grain yield, number of spikelets per panicle, heading date and plant height in the $BC_3F_2$ random population.

FIG. 3a is a graph that shows mapping of a recombinant inbred line population; FIG. 3b is a graph that shows mapping using $BC_3F_2$ small population; and FIG. 3c is a graph that shows accurate mapping using an extremely recessive individual plant. Numerals on the left of the chromosome represent the physical distance between two markers, and numerals in the brackets following the markers on the right represent the time of recombination of the gene with the respective marker.

FIG. 5 shows the phenotypes of the near isogenic lines and transgenic individual plants of the present invention.

DETAILED DESCRIPTION OF THE INVENTION

Figure 1:
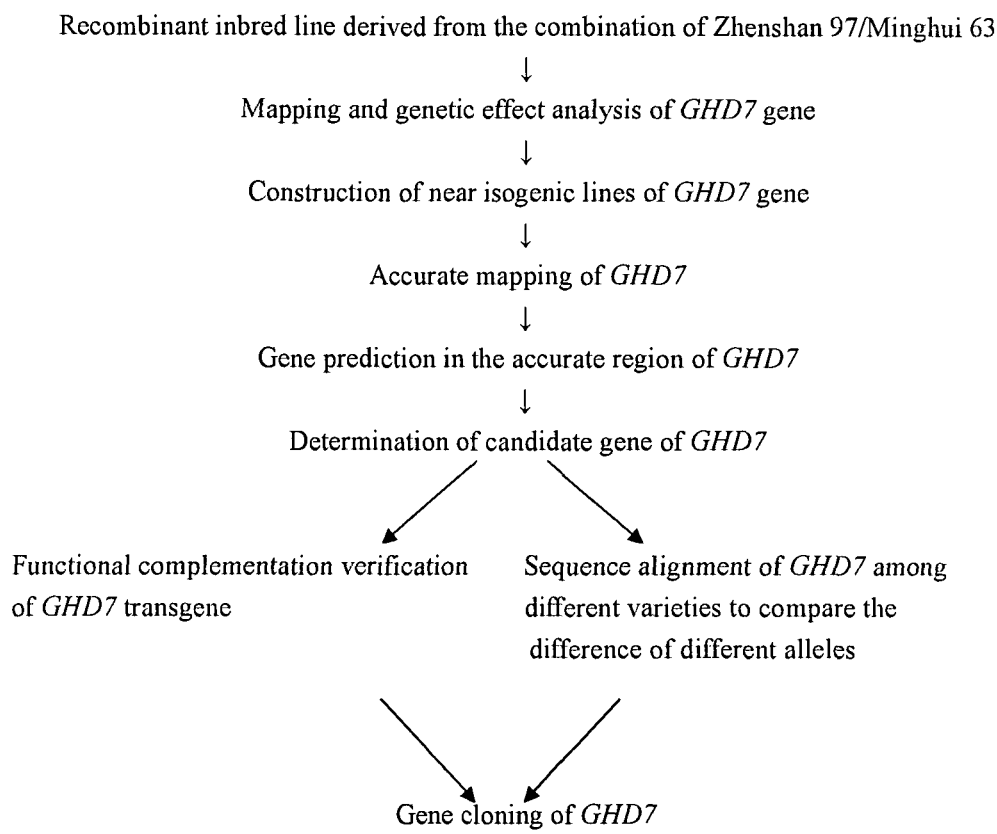
FIG. 1 is the overall technology scheme of the present invention.

According to the technology scheme in FIG. 1, a plant comprising Minghui 63 Ghd7 allele and having a genetic background most similar to that of Zhenshan 97, i.e. No. 50 inbred line RIL50, was selected from the recombinant inbred line population derived from the combination of Zhenshan 97 and Minghui 63 (See Xing Yongzhong et. al., Mapping and Separation of Plant Height Gene and Heading Date Gene in Rice, Journal of Integrative Plant Biology, 2001, 43(7): 721-726). The selected plant was used to conduct backcrossing with Zhenshan 97 (as the recurrent parent) for three generations in succession followed by inbreeding to construct near isogenic lines of the Ghd7 gene. Ghd7 was mapped and its genetic effect analyzed using a random population comprising 190 $BC_3F_2$ individual plants. Further analysis of 1,082 extremely early heading, short stalk and small ear individual plants from 8,400 individual plants using common SSR markers in the target region finally mapped Ghd7 to a region between C39 and RM3859, the two markers having a genetic distance of 0.4 cM but a physical distance up to 2,300 kb. Sequence analysis using Nipponbare, whose genome has been completely sequenced, and 93-11 (a medium indica variety bred by the Agricultural Science Research Institute in Lixia River Area, Jiangsu Province) resulted in the prediction that there exists in the region a gene with CCT domain and the gene was determined to be the candidate gene for Ghd7. An 8,1725 bp sequence fragment comprising Ghd7 gene was isolated from the BAC library of Minghui 63 and the fragment was ligated into the binary plasmid vector pCAMBIA1301 (a publicly reported and used plasmid from Australia). Overexpression and sense transformation of the vector into receptor plants Hejing 19, Mudanjiang 8 and Zhenshan 97 resulted in transgenic individual plants that exhibited the expected trait changes, i.e., markedly increased yield, enlarged ear size, delayed heading date and elevated plant height. These phenotypes were extremely similar to those of the two homozygous genotypes of Ghd7 near isogenic lines, demonstrating that this candidate gene is just Ghd7 which is absent in Zhenshan 97. Primers were designed based on the Ghd7 sequence and the full-length cDNA sequence of Ghd7, 1,014 bp in length, was isolated using RACE technology. Sequence alignment of the 5.5 kb sequence comprising the promoter and whole gene revealed that the first exon of the four large ear varieties (as the growth stage in Wuhan, China was long, the plant height was higher and the rice ear was larger) had a common variation compared with the two small ear varieties, i.e. GAG encoding glutamic acid is replaced with the stop codon (TGA). Treatment of the negative and positive transgenic individual plants along with the near isogenic lines of the two homozygous genotypes under short-day and long-day conditions reveals the following discoveries: the expression of Ghd7 under long-day condition was enhanced as compared to short-day condition; Minghui 63 homozygous genotype plants exhibited a markedly delayed heading date, elevated plant height and enlarged ear size and increased yield under long-day condition. However, under short-day condition, the phenotypes of the genotypes differed insignificantly and were similar to that of Zhenshan 97.

The following Examples further describe the present invention. They illustrate the methods for separation and cloning of Ghd7 gene and genetic transformation as well as the methods for the detection of the sequence difference between Ghd7 alleles by sequence alignment, and the expression of Ghd7 gene under long-day and short-day conditions. Based on the following description and Examples, those skilled in the art can determine the essential features of the present invention and are able to make various changes and modifications to the present invention to apply it to different uses and conditions without departing from the concept and scope of the present invention.

Example 1

Construction of Ghd7 Near Isogenic Lines

1. Backcrossing and Selection

Figure 3:
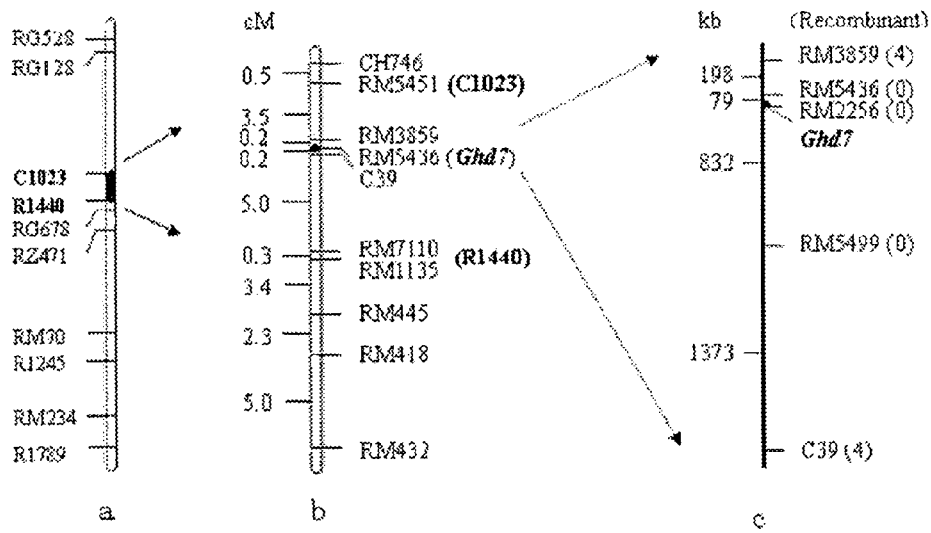
FIG. 3. Mapping of Ghd7 in the genetic linkage map, the genetic unit being in cM.
Figure 4:
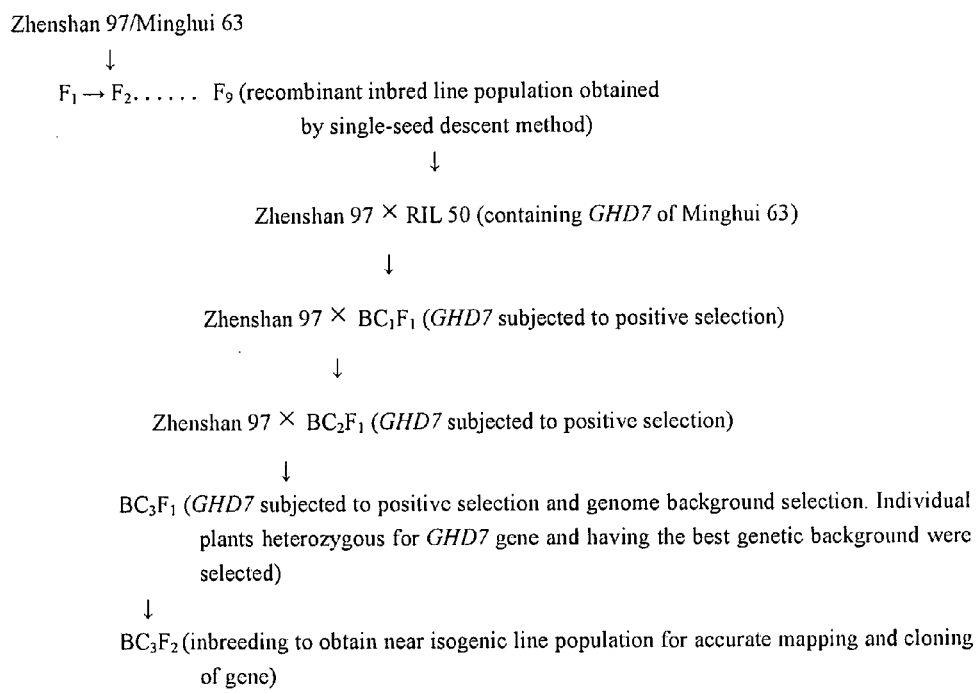
FIG. 4 is the flowchart of construction of the near isogenic lines of the present invention. Zhenshan 97 was used as the female parent in backcrossing.

As shown in FIG. 3a, based on the QTL mapping result of the recombinant inbred line population derived from Zhenshan 97 and Minghui 63 and in conjunction with marker genotype, the inbred line RIL50 comprising the Ghd7 allele of Minghui 63 and having a genetic background 70% identical to that of Zhenshan 97 was selected as the female parent to conduct backcrossing with Zhenshan 97 three times in succession, followed by inbreeding one time to obtain $BC_3F_2$ (FIG. 4). The $BC_1F_1$ and $BC_2F_1$ generations were only subjected to positive selection for Ghd7, that is, an individual plant with the target region having the Zhenshan 97/Minghui 63 heterozygous genotype was selected for the next round of backcrossing. The $BC_3F_1$ generation, in addition to positive selection, was subjected to scanning of the genetic background outside the target region so that individual plants with a genetic background closest to that of Zhenshan 97 were selected for the subsequent experiments. By referring to published rice genetic linkage maps (Temnykh et. al., 2000, Theor. Appl. Genet. 100:697-712; Temnykh et. al., 2001, Genome Res. 11:1441-1452), 150 pairs of SSR markers showing polymorphism among the parents and evenly distributed on 12 rice chromosomes were selected for the screening of genetic background. An individual plant with a genetic background closest to that of Zhenshan 97 ($BC_3F_1$) was finally selected, whose RM5451 and RM445 markers (see the Gramene website) showed a genotype of heterozygous Zhenshan 97/Minghui 63, while only 7% (10 pairs) of the 150 pairs of the SSR markers showed a genotype of heterozygous Zhenshan 97/Minghui 63, and the rest showed a genotype of homozygous Zhenshan 97/Minghui 63. The progenies of said individual plant ($BC_3F_2$ and $BC_3F_3$) were used in the subsequent accurate mapping and cloning of genes.

2. SSR Method

The standard PCR protocol refers to Sambrook, J. et al., Molecular Cloning: A Laboratory Manual, 3rd ed., (translated by Jin Dongyan et al.), Science Press, 2002. The PCR used a 200 reaction system which comprised 20-50 ng DNA template, 10 mM Tris-HCl, 50 mM KCl, 0.1% Triton X-100, 1.8 mM $MgCl_2$, 0.1 mM dNTP, 0.2 μM primers (for primers for the above-said RM282 and RM16, refer to the Gramene website) and 1 U Taq DNA polymerase. Conditions for PCR were: predenaturing at 94° C. for 4 min; 94° C. 1 min, 55° C. 1 min, 72° C. 1 min, 34 cycles; elongation at 72° C. for 10 min. PCR products were isolated on a 6% polyacrylamide gel and then silver-stained (Bassam et. al., 1991, Anal Biochem 196 80-83).

Example 2

Mapping and Effect Evaluation of Ghd7 in the Random Population

1. Measurement of phenotype

"Heading date" as used herein refers to the number of days from the day of seeding to the day when an individual plant grows its first ear, i.e. heading date of an individual plant. "Plant height" as used herein refers to the height from the surface of the field to the top of the highest ear of an individual plant, i.e. plant height of an individual plant, "Number of spikelets per panicle" as used herein refers to the quotient of the total number of grains (including the number of filled grains and the number of unfilled grains) of an individual plant divided by the number of effective ears of the plant. "Yield" as used herein refers to the mass of filled grains of an individual plant after natural drying of the grains, i.e. yield of grains.

Figure 2A:
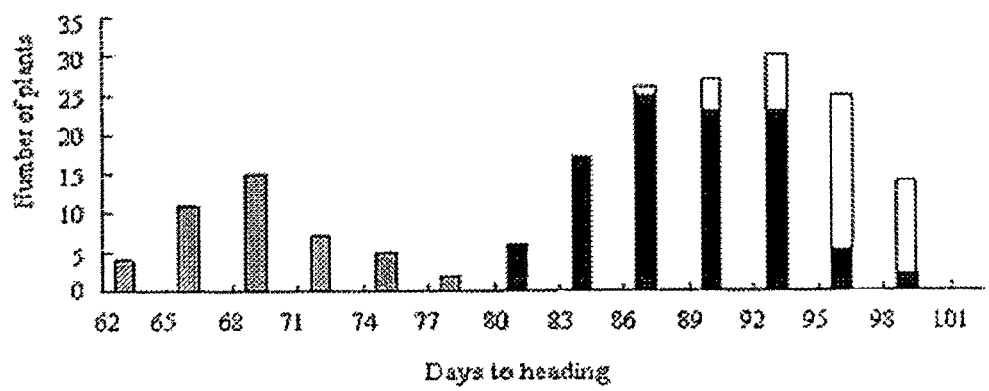
FIG. 2a shows the frequency distribution of heading date.
Figure 2B:
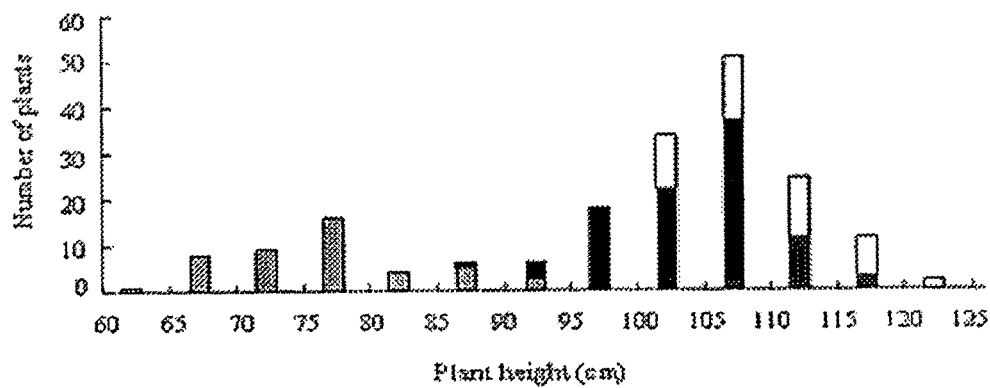
FIG. 2b shows the frequency distribution of plant height and FIG. 2c shows the frequency distribution of number of spikelets per panicle. The grey, black and white bars in the figures represent Zhenshan 97 genotype, heterozygous genotype and Minghui 63 genotype in Ghd7 site. These three genotypes of Ghd7 were inferred through progeny test.
Figure 2C:
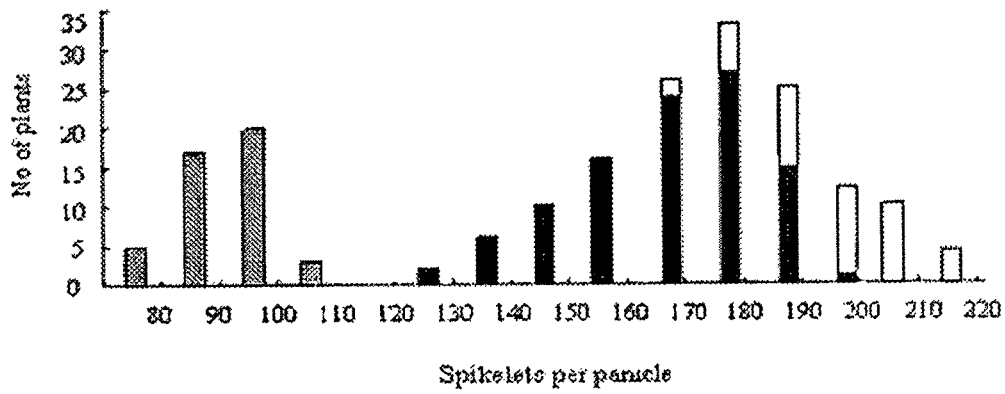

From among the $BC_3F_2$ population derived from a $BC_3F_1$ individual plant, 190 individual plants were randomly selected to form a random population. Each individual plant in the Zhenshan 97 population, Minghui 63 population and the random population was evaluated for its heading date, plant height, number of spikelets per panicle and yield. Results showed that all traits were significantly different between the two parents (Table 1). In the random population, the number of spikelets per panicle showed a discontinuous distribution, and taken 110-120 grains as the dividing line, the population may be divided into two types, i.e. large ear type and small ear type (table 1 and FIG. 2c). Heading date, plant height and yield all showed a continuous bimodal distribution (FIGS. 2a, 2b and 2c). Moreover, yield showed a most significantly positive correlation with plant height, heading date and number of spikelets per panicle, that is, high yield plants had a higher plant height, a later day of heading and a larger number of spikelets per panicle as compared to low yield plants. For simplicity of description, in the present invention, the type having a larger number of spikelets per panicle is referred to as large ear type, and the type having a smaller number of spikelets per panicle is referred to as small ear type.

TABLE 1

Values of the phenotypes in the two parents and in the large and small ear types in the random population

| | Parents (mean ± SD) | | Large ear type | | Small ear type | |
|---|---|---|---|---|---|---|
| Traits | Zhenshan 97 | Minghui 63 | Mean ± SD | Range | Mean ± SD | Range |
| Yield of an individual plant (g) | 19.6 ± 1.6 | 29.9 ± 2.1 | 25.7 ± 4.0 | 16.5-39.4 | 10.5-25.3 | 17.5 ± 2.8 |
| Number of spikelets per panicle | 109.2 ± 6.4 | 148.6 ± 9.5 | 174.8 ± 27.7 | 121.9-216.7 | 90.2 ± 11.3 | 74.9-109.2 |
| Heading date (day) | 60.4 ± 1.3 | 89.2 ± 1.5 | 81.9 ± 7.3 | 71.3-92.4 | 60.7 ± 1.8 | 59.1-62.7 |
| Plant height (cm) | 79.4 ± 2.1 | 107.4 ± 2.5 | 109.3 ± 8.9 | 98.1-129.3 | 80.0 ± 5.6 | 70.1-91.7 |

2. QTL Mapping and Effect Evaluation of Ghd7

Twenty one SSR markers were selected from the QTL region between C1023-R1440 (FIG. 3a), and nine PCR markers and one RFLP marker were obtained which showed polymorphism between Zhenshan 97 and Minghui 63. The random population of near isogenic lines was analyzed for marker genotype. Mapmaker/Exp 3.0 software (Lincoln et. al. 1992, Whitehead Institute Technical Report, Whitehead Institute, Cambridge, Mass., USA) was used to construct a local genetic linkage map for the Ghd7 region (FIG. 3b). Yield, number of spikelets per panicle, heading date and plant height of individual plants in the random population were QTL mapped using region mapping method Mapmaker/QTL 1.1, with a LOD value of 3.0 as the threshold for QTL detection. Results in table 2 showed that a QTL found in the region from RM3859 to C39 had effects on yield, number of spikelets per panicle, heading date and plant height of individual plants, and accounted for 43.2%, 74.2%, 91.8% and 88.9% of the phenotypic variation for these traits, respectively. The genotype of Minghui 63 contributed to the increase in yield, number of spikelets per panicle, heading date and plant height of individual plants. The QTL exhibited a partial dominant effect on several different traits. This indicated that superior alleles could be targeted through marker-assisted selection to modify rice varieties. Moreover, the dominant homozygous genotype is the relatively ideal genotype.

TABLE 2

Effects of the QTL in the region from RM3859 to C39 on yield, number of spikelets per panicle, heading date and plant height

| Traits | LOD | A[a] | D[b] | D/A | $R^2$ (%)[c] |
|---|---|---|---|---|---|
| Yield (gram) | 22.3 | 4.4 | 2.7 *** | 0.61 | 43.2 |
| Number of spikelets per panicle | 56.1 | 59.8 | 28.3 *** | 0.47 | 74.2 |
| Heading date (day) | 102.9 | 12.3 | 4.0 * | 0.33 | 91.8 |
| Plant height (cm) | 76.7 | 18.8 | 12.3 ** | 0.65 | 88.9 |

[a] Additive effect of Minghui 63 allele;
[b] Dominance effect of Minghui 63 allele;
*,  and * refer to significance level at P < 0.01, 0.001 and 0.0001 (t-test);
[c] Percentage of total phenotypic variance explained by the QTL.

4. Progeny Test

Each individual plant in said random population was cultivated into 20 families ($BC_3F_3$ generation) for progeny test. It was found that, among the 190 plants, 45 plants had progenies that showed phenotypes of small ear, early heading, short stalk and low yield, 43 plants had progenies that showed phenotypes of large ear, late heading, tall stalk and high yield, and the remaining 102 plants had progenies that exhibited segregation in the four target traits. Chi-square test showed that these three groups of plants followed the segregation ratio of 1:2:1 for a single Mendelian factor ($\chi^2$=1.07, P>0.05), indicating that in this $BC_3F_2$ population the four traits were controlled by a major gene, and that the large ear allele was dominant over the small ear allele. Since these three groups as exhibited by the progenies corresponded to the three genotypes of the $BC_3F_2$ individual plants at Ghd7 locus: Minghui 63 homozygous genotype (large ear), Zhenshan 97 homozygous genotype (small ear) and heterozygous genotype (segregation of large ear and small ear), therefore Ghd7 as a marker was directly mapped to a 0.4 cM region between SSR marker RM3859 and RFLP marker C39, and Ghd7 was cosegregated with RM5436 (FIG. 3c).

Example 3

Accurate Mapping of Ghd7 and Determination of Candidate Gene

1. Screening of Recombinant Individual Plants and Accurate Mapping of Ghd7

In order to further narrow down the region comprising Ghd7, from among the 8,400 $BC_3F_2$ plants derived from a $BC_3F_1$ individual plant, 1,082 individual plants heading the earliest and showing short stalks and small ears were selected and used for the screening of recombinant individual plants. On the basis of mapping of random small population, 5 SSR markers and 1 RFLP marker (FIG. 3b) in the 8 cM region comprising Ghd7 were selected to screen these 1,082 individual plants.

Firstly, 1,082 individual plants were screened with SSR markers RM5431 and RM445 to give 66 and 94 recombinant individual plants (160 in total) respectively. Then, these 160 recombinant individual plants were analyzed using the following four markers: RM3859, RM5436, RM5499, C39 and RM7110. It was found that there were 8 recombinant individual plants wherein it was in the region between RM3859 and C39, and respectively 4 recombinant individual plants in the region between RM3859 and Ghd7 and in the region between C39 and Ghd7. And RM5436 and RM5499 were both cosegregated with Ghd7 (FIG. 3c). Therefore, Ghd7 was finally mapped to the region between RM3859 and C39. This region corresponded to the physical scope of about 2,300 kb in the Nipponbare genome sequence and was cosegregated with the 920 kb region (FIG. 3c).

2. Determination of Candidate Gene

The 0.4 cM genetic distance of the region comprising Ghd7 corresponded to a physical distance of 2,300 kb, which indicated the presence of severe recombinant inhibition in the target region. This was associated with the region near the centromere where the gene located. Ghd7 was cosegregated with the 920 kb region, which indicated that map-based cloning was incapable of further narrowing down the gene region. Therefore, the candidate gene was determined by use of the candidate gene approach. All possible genes were predicted based on the corresponding 2,300 kb region sequence of Nipponbare. It was found that there were more than 450 genes in the region, among which one gene had CCT (CONSTANS (CO), CO-LIKE and TIMING OF CAB1 (TOC1)) conserved domain and was reported to be associated with the flowering period of Arabidopsis and rice, therefore it was prioritized as the candidate gene for Ghd7.

Example 5

Transgenic Complementation Test for Ghd7

Based on the predicted candidate gene sequence, three pairs of PCR primers as shown in Table 3 were designed to screen the DNA pool of BAC library of Minghui 63, and clones containing the candidate gene were selected. Positive clones were excised using restriction endonucleases BamHI and EcoRI and subcloned to obtain an 8,175 bp fragment which contains a 2,261 kb sequence upstream of transcription initiation site and a 3,255 kb sequence downstream of transcription termination site.

Figure 6:
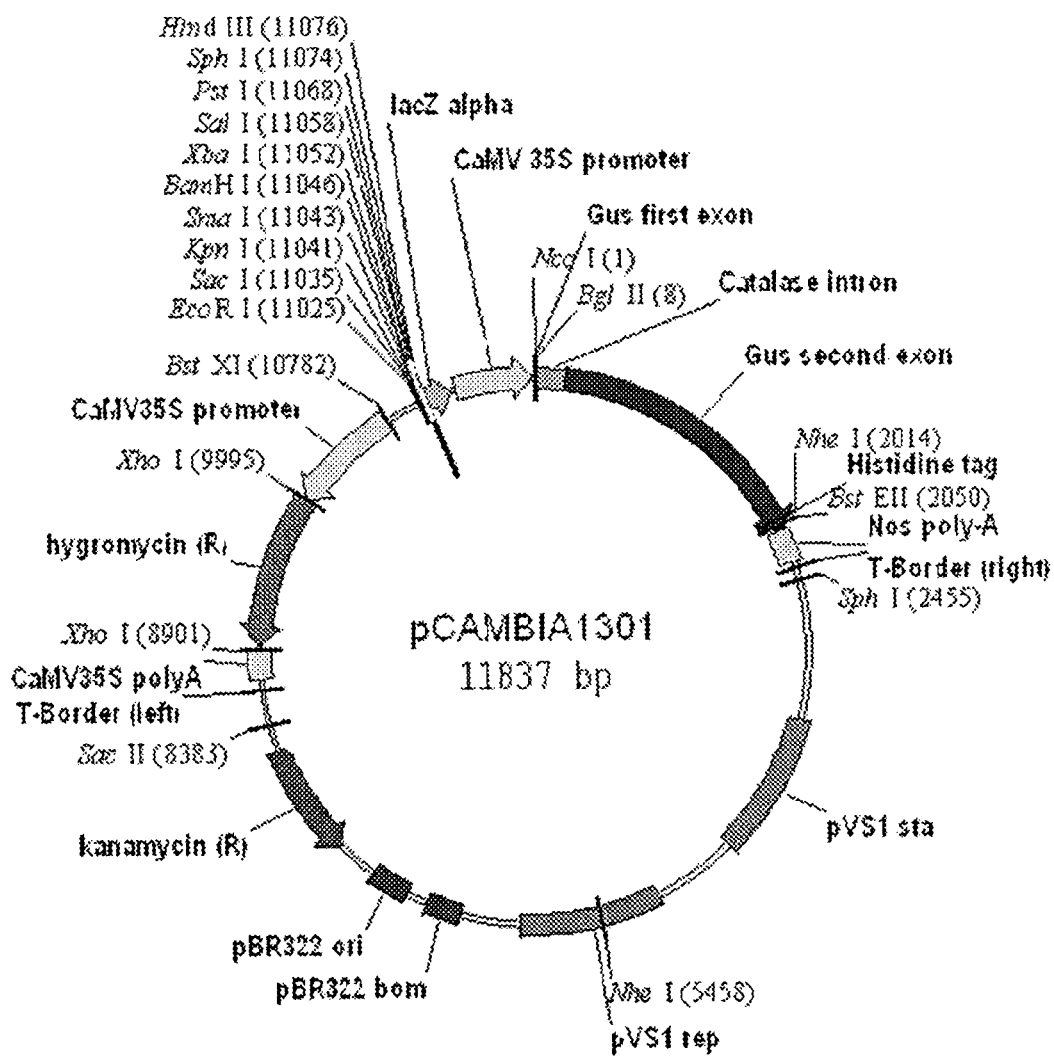
FIG. 6 is the structural diagram of binary vector pCAMBIA1301.

This fragment was ligated into the binary vector pCAM-BIA1301 and transgenic rice plants were obtained using transgene method. More specifically, the transgenic rice plants were obtained as follows:

The selected Minghui 63 BAC 60F11 was excised using restriction endonucleases BamHI and EcoRI, and a fragment about 8 kb in length was isolated on 0.8% agarose. This fragment was ligated into the binary vector pCAMBIA1301 (the diagram of the vector is shown in FIG. 6) and then positive clones were screened using the primers as shown in Table 3. The obtained clone was sequenced using the primers as shown in Table 3 to confirm that the fragment where the gene resides was ligated into the vector. The thus obtained correct cloned plasmid was introduced into the rice varieties of Zhonghua Hejiang 19 and Mudanjiang 8 using a rice genetic transformation system mediated by Agrobacterium. A transgenic plant was obtained through precultivation, infestation, co-cultivation, screening of the callus with hygromycin resistance, differentiation, rooting, seedling establishment and transplanting. The rice (japonica rice subspecies) genetic transformation system mediated by Agrobacterium was optimized on the basis of the method reported by Hiei, et al. (See "Efficient transformation of rice, Oryza sativa L., mediated by Agrobacterium and sequence analysis of the boundaries of the T-DNA", 1994, Plant Journal 6:271-282).

The media and their method of preparation for and the main steps of the genetic transformation of the present invention were as follows:

(1) Abbreviations of Reagents and Solutions

The abbreviations of phytohormones used in culture media of the present invention were as follows: 6-BA (6-Benzylaminopurine); CN (Carbenicillin); KT (Kinetin); NAA (Napthalene acetic acid); IAA (Indole-3-acetic acid); 2,4-D (2,4-Dichlorophenoxyacetic acid); AS (Acetosringone); CH (Casein Enzymatic Hydrolysate); HN (Hygromycin B); DMSO (Dimethyl Sulfoxide); N6max (N6 macroelements solution); N6mix (N6 microelements solution); MSmax (MS macroelements solution); MSmix (MS microelements solution)

(2) Formulae of Primary Solutions

1) Preparation of N6 Macroelements Mother Solution (Prepared as 10× Concentrate):

| | |
|---|---|
| $KNO_3$ | 28.3 g |
| $KH_2PO_4$ | 4.0 g |
| $(NH_4)_2SO_4$ | 4.63 g |
| $MgSO_4 \cdot 7H_2O$ | 1.85 g |
| $CaCl_2 \cdot 2H_2O$ | 1.66 g |

These compounds were dissolved in succession and then the volume was brought to 1000 ml with distilled water at room temperature.

2) Preparation of N6 Microelements Mother Solution (Prepared as 10× Concentrate):

| | |
|---|---|
| KI | 0.08 g |
| $H_3BO_3$ | 0.16 g |
| $MnSO_4 \cdot 4H_2O$ | 0.44 g |
| $ZnSO_4 \cdot 7H_2O$ | 0.15 g |

These compounds were dissolved and then the volume was brought to 1000 ml with distilled water at room temperature.

3) Preparation of Ferric Salt (Fe$_2$EDTA) Stock Solution (Prepared as 10× Concentrate):

3.73 g Na$_2$EDTA.2H$_2$O and 2.78 g FeSO$_4$.2H$_2$O were dissolved, mixed and brought to 1000 ml with distilled water. The resulting solution was kept in 70° C. water bath for 2 h and stored at 4° C. for use.

4) Preparation of Vitamins Stock Solution (Prepared as 10× Concentrate):

| | |
|---|---|
| Nicotinic acid | 0.1 g |
| Vitamin B1 (Thiamine HCl) | 0.1 g |
| Vitamin B6 (Pyridoxine HCl) | 0.1 g |
| Glycine | 0.2 g |
| Inositol | 10 g |

Distilled water was added to bring the volume to 1000 ml and the resulting solution was stored at 4° C. for use.

5) Preparation of MS Macroelements Mother Solution (MS-Max Mother Solution) (Prepared as 10× Concentrate):

| | |
|---|---|
| NH$_4$NO$_3$ | 16.5 g |
| KNO$_3$ | 19.0 g |
| KH$_2$PO$_4$ | 1.7 g |
| MgSO$_4$ | 3.7 g |
| CaCl$_2$ | 4.4 g |

These compounds were dissolved at room temperature and then the volume was brought to 1000 ml with distilled water.

6) Preparation of MS Microelements Mother Solution (MS-mix Mother Solution) (Prepared as 10× Concentrate):

| | |
|---|---|
| MnSO$_4$•4H$_2$O | 2.23 g |
| ZnSO$_4$•7H$_2$O | 0.86 g |
| H$_3$BO$_3$ | 0.62 g |
| KI | 0.083 g |
| Na$_2$MoO$_4$•2H$_2$O | 0.025 g |
| CuSO$_4$•5H$_2$O | 0.0025 g |
| CoCl$_2$•6H$_2$O | 0.0025 g |

These compounds were dissolved at room temperature and then the volume was brought to 1000 ml with distilled water.

7) Preparation of 2,4-D stock solution (1 mg/ml):

100 mg 2,4-D was weighed and dissolved in 1 ml 1 N potassium hydroxide for 5 minutes, then 10 ml distilled water was added for complete dissolution. The resulting solution was brought to 100 ml and stored at room temperature.

8) Preparation of 6-BA Stock Solution (1 mg/ml):

100 mg 6-BA was weighed and dissolved in 1 ml 1 N potassium hydroxide for 5 minutes, then 10 ml distilled water was added for complete dissolution. The resulting solution was brought to 100 ml and stored at room temperature.

9) Preparation of NAA Stock Solution (1 mg/ml):

100 mg NAA was weighed and dissolved in 1 ml 1 N potassium hydroxide for 5 minutes, then 10 ml distilled water was added for complete dissolution. The resulting solution was brought to 100 ml and stored at 4° C. for use.

10) Preparation of IAA Stock Solution (1 mg/ml):

100 mg IAA was weighed and dissolved in 1 ml 1 N potassium hydroxide for 5 minutes, then 10 ml distilled water was added for complete dissolution. The resulting solution was brought to 100 ml and stored at 4° C. for use.

11) Preparation of Glucose Stock Solution (0.5 g/ml):

125 g glucose was weighed and dissolved with distilled water. The resulting solution was brought to 250 ml, sterilized and stored at 4° C. for use.

12) Preparation of AS Stock Solution:

0.392 g AS was weighed and dissolved with 10 ml DMSO. The resulting solution was dispensed in 1.5 ml centrifuge tubes and stored at 4° C. for use.

13) Preparation of 1 N Potassium Hydroxide Stock Solution:

5.6 g potassium hydroxide was weighed and dissolved with distilled water. The resulting solution was brought to 100 ml and stored at room temperature for use.

(3) Culture Media Formulae for Genetic Transformation of Rice

1) Induction Culture Medium:

| | |
|---|---|
| N6max mother solution (use the prepared 10X concentrate, the same below) | 100 ml |
| N6mix mother solution (use the prepared 100X concentrate, the same below) | 10 ml |
| Fe$^{2+}$EDTA stock solution (use the prepared 100X concentrate, the same below) | 10 ml |
| Vitamins stock solution (use the prepared 100X concentrate, the same below) | 10 ml |
| 2,4-D stock solution (use the prepared stock solution as described above) | 2.5 ml |
| Proline | 0.3 g |
| CH | 0.6 g |
| Sucrose | 30 g |
| Phytagel | 3 g |

Distilled water was added to a volume of 900 ml, and the pH value was adjusted to 5.9 with 1 N potassium hydroxide. The resulting mixture was boiled and brought to 1000 ml. The resulting medium was dispensed into 50 ml Erlenmeyer flasks (25 ml/flask), and the flasks were sealed and sterilized using conventional methods (e.g., sterilized at 121° C. for 25 minutes. The method of sterilization for the following media was the same as that of this medium).

2) Secondary Culture Medium:

| | |
|---|---|
| N6max mother solution (10X) | 100 ml |
| N6mix mother solution (100X) | 10 ml |
| Fe$^{2+}$EDTA stock solution (100X) | 10 ml |
| Vitamins stock solution (100X) | 10 ml |
| 2,4-D stock solution | 2.0 ml |
| Proline | 0.5 g |
| CH | 0.6 g |
| Sucrose | 30 g |
| Phytagel | 3 g |

Distilled water was added to a volume of 900 ml, and the pH value was adjusted to 5.9 with 1 N potassium hydroxide. The resulting mixture was boiled and brought to 1000 ml. The resulting medium was dispensed into 50 ml Erlenmeyer flasks (25 ml/flask), and the flasks were sealed and sterilized as above.

3) Pre-Culture Medium:

| | |
|---|---|
| N6max mother solution (10X) | 12.5 ml |
| N6mix mother solution (100X) | 1.25 ml |
| Fe$^{2+}$EDTA stock solution (100X) | 2.5 ml |
| Vitamins stock solution (100X) | 2.5 ml |
| 2,4-D stock solution | 0.75 ml |
| CH | 0.15 g |

-continued

| | |
|---|---|
| Sucrose | 5 g |
| Agarose | 1.75 g |

Distilled water was added to a volume of 250 ml, and the pH value was adjusted to 5.6 with 1 N potassium hydroxide. The resulting medium was sealed and sterilized as above.

Prior to use, the medium was heated to dissolve and 5 ml glucose stock solution and 250 μl AS stock solution were added. The resulting medium was dispensed into the culture dishes (25 ml/dish).

4) Co-Culture Medium:

| | |
|---|---|
| N6max mother solution (10X) | 12.5 ml |
| N6mix mother solution (100X) | 1.25 ml |
| $Fe^{2+}$EDTA stock solution (100X) | 2.5 ml |
| Vitamins stock solution (100X) | 2.5 ml |
| 2,4-D stock solution | 0.75 ml |
| CH | 0.2 g |
| Sucrose | 5 g |
| Agar powder | 1.75 g |

Distilled water was added to a volume of 250 ml, and the pH value was adjusted to 5.6 with 1 N potassium hydroxide. The resulting medium was sealed and sterilized as above.

Prior to use, the medium was heated to dissolve and 5 ml glucose stock solution and 250 μl AS stock solution were added. The resulting medium was dispensed into the culture dishes (25 ml/dish).

5) Suspension Medium:

| | |
|---|---|
| N6max mother solution (10X) | 5 ml |
| N6mix mother solution (100X) | 0.5 ml |
| $Fe^{2+}$EDTA stock solution (100X) | 0.5 ml |
| Vitamins stock solution (100X) | 1 ml |
| 2,4-D stock solution | 0.2 ml |
| CH | 0.08 g |
| Sucrose | 2 g |

Distilled water was added to a volume of 100 ml, and the pH value was adjusted to 5.4. The resulting medium was dispensed into two 100 ml Erlenmeyer flasks and the flasks were sealed and sterilized as above.

Prior to use, 1 ml sterile glucose stock solution and 100 μl AS stock solution were added.

6) Selective Medium:

| | |
|---|---|
| N6max mother solution (10X) | 25 ml |
| N6mix mother solution (100X) | 2.5 ml |
| $Fe^{2+}$EDTA stock solution (100X) | 2.5 ml |
| Vitamins stock solution (100X) | 2.5 ml |
| 2,4-D stock solution | 0.625 ml |
| CH | 0.15 g |
| Sucrose | 7.5 g |
| Agar powder | 1.75 g |

Distilled water was added to a volume of 250 ml, and the pH value was adjusted to 6.0. The resulting medium was sealed and sterilized as above.

Prior to use, the medium was dissolved and 250 μl HN (50 mg/ml) and 400 μl CN (250 mg/ml) were added. The resulting medium was dispensed into the culture dishes (25 ml/dish). (Note: for the first selective medium, the concentration of ampicillin is 400 mg/L, and for the second and later selective media, the concentration of ampicillin is 250 mg/L).

7) Pre-Differentiation Medium:

| | |
|---|---|
| N6max mother solution (10X) | 25 ml |
| N6mix mother solution (100X) | 2.5 ml |
| $Fe^{2+}$ EDTA stock solution (100X) | 2.5 ml |
| Vitamins stock solution (100X) | 2.5 ml |
| 6-BA stock solution | 0.5 ml |
| KT stock solution | 0.5 ml |
| NAA stock solution | 50 μl |
| IAA stock solution | 50 μl |
| CH | 0.15 g |
| Sucrose | 7.5 g |
| Agar powder | 1.75 g |

Distilled water was added to a volume of 250 ml, and the pH value was adjusted to 5.9 with 1N potassium hydroxide. The resulting medium was sealed and sterilized as above.

Prior to use, the medium was dissolved and 250 μl HN (50 mg/ml) and 250 μl CN (250 mg/ml) were added. The resulting medium was dispensed into the culture dishes (25 ml/dish).

8) Differentiation Medium:

| | |
|---|---|
| N6max mother solution (10X) | 100 ml |
| N6mix mother solution (100X) | 10 ml |
| $Fe^{2+}$ EDTA stock solution (100X) | 10 ml |
| Vitamins stock solution (100X) | 10 ml |
| 6-BA stock solution | 2 ml |
| KT stock solution | 2 ml |
| NAA stock solution | 0.2 ml |
| IAA stock solution | 0.2 ml |
| CH | 1 g |
| Sucrose | 30 g |
| Phytagel | 3 g |

Distilled water was added to a volume of 900 ml, and the pH value was adjusted to 6.0 with 1N potassium hydroxide.

The resulting mixture was boiled and brought to 1000 ml. The resulting medium was dispensed into 50 ml Erlenmeyer flasks (50 ml/flask), and the flasks were sealed and sterilized as above.

9) Rooting Medium:

| | |
|---|---|
| MSmax mother solution (10X) | 50 ml |
| MSmix mother solution (100X) | 5 ml |
| $Fe^{2+}$ EDTA stock solution (100X) | 5 ml |
| Vitamins stock solution (100X) | 5 ml |
| Sucrose | 20 g |
| Phytagel | 3 g |

Distilled water was added to a volume of 900 ml, and the pH value was adjusted to 5.8 with 1N potassium hydroxide.

The resulting mixture was boiled and brought to 1000 ml. The resulting medium was dispensed into the rooting tubes (25 ml/tube), and the tubes were sealed and sterilized as above.

(4) Steps of Genetic Transformation Mediated by *Agrobacterium*

3.1 Callus Induction (1) Mature rice seeds of Hejiang 19 and Mudanjiang 8 were husked, and then were successively treated with 70% alcohol for 1 minute and surface-disinfected with 0.15% $HgCl_2$ for 15 minutes;

(2) The seeds were washed with sterilized water for 4-5 times;

(3) The seeds were put onto the induction medium;

(4) The seeded medium was placed in darkness for 4-week culture at 25±1° C.

3.2 Callus Subculture

The bright yellow, compact and relatively dry embryogenic callus was selected, put onto the secondary culture medium, and cultured in darkness for 2 weeks at 25±1° C.

3.3 Pre-Culture

The compact and relatively dry embryogenic callus was selected, put onto the pre-culture medium, and cultured in darkness for 2 weeks at 25±1° C.

3.4 Agrobacterium Culture (1) Agrobacterium EHA105 (a publicly used Agrobacterium strain commercially available from Cambia Co.) was pre-cultured on the LA culture medium with corresponding resistance selection (for the preparation of LA culture medium, see Sambrook, J. et al., Molecular Cloning: A Laboratory Manual, 3rd ed., (translated by Jin Dongyan et al.), Science Press, 2002, Beijing) at 28° C. for 2 days;

(2) The Agrobacterium was transferred to the suspension medium and cultured on the shaking table at 28° C. for 2-3 hours.

3.5 Agrobacterium Infestation (1) The pre-cultured callus was transferred into a sterilized bottle;

(2) The Agrobacterium suspension was adjusted to $OD_{600}$ 0.8-1.0;

(3) The callus was immersed in the Agrobacterium suspension for 30 minute;

(4) The callus was transferred onto a sterilized filter paper and dried, and then put onto the co-culture medium for 3-day culture at 19-20° C.

3.6 Washing and Selective Culture of Callus (1) The callus was washed with sterilized water until no Agrobacterium was observed;

(2) The callus was immersed in sterilized water containing 400 mg/L carbenicillin (CN) for 30 minutes;

(3) The callus was transferred onto a sterilized filter paper and dried;

(4) The callus was transferred onto the selective medium and selectively cultured for 2-3 times, 2 weeks for each time.

3.7 Differentiation (1) The resistant callus obtained was transferred to the pre-differentiation medium, and cultured in darkness for 5-7 weeks;

(2) The callus obtained from the pre-differentiation culture was transferred to the differentiation medium and cultured at 26° C. under light.

4.8 Rooting (1) The roots of the callus generated during differentiation were cut off;

(2) The callus was then transferred to the rooting medium, and cultured at 26° C. under light for 2-3 weeks.

4.9 Transplantation

The residual medium on the roots of the callus was washed off, and the seedlings with good roots were transferred into the greenhouse. The greenhouse was maintained moisturized in the first few days.

Figure 5A:
FIG. 5a shows plants of the near isogenic lines, which are, from the left to the right, Zhenshan 97, Zhenshan 97-Zhenshan 97 Ghd7, Zhenshan 97-hybrid Ghd7, Zhenshan 97-Minghui 63 Ghd7, Minghui 63, respectively.
Figure 5B:
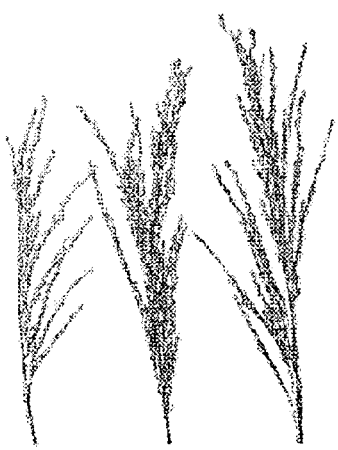
FIG. 5b shows the rice ears, which are, from the left to the right, Zhenshan 97-Zhenshan 97 Ghd7, Zhenshan 97-hybrid Ghd7, Zhenshan 97-Minghui 63 Ghd7 genotypes respectively.
Figure 5C:
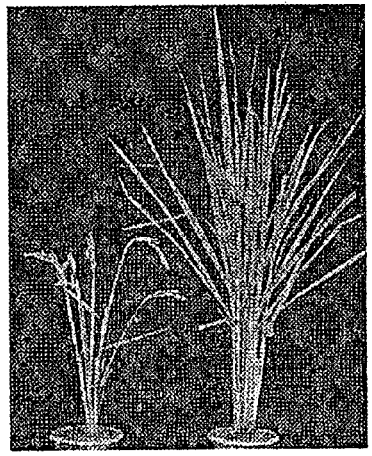
FIG. 5c shows the Ghd7 transgenic plants, wherein the left represents the negative plant of Hejiang 19 and the right represents the positive plant.
Figure 5D:
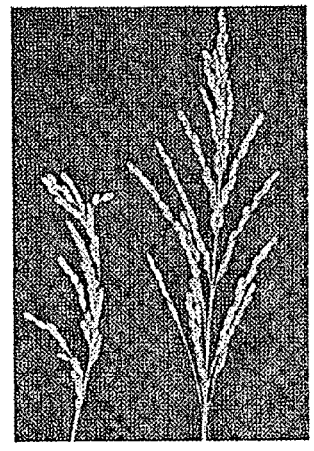
FIG. 5d shows the rice ears of the transgenic plants, wherein the left represents the rice ear of the negative plant of Hejiang 19 and the right represents the rice ear of the positive plant.

Transformation of the Japonica varieties of Hejiang 19 and Mudanjiang 8 yielded the T0 generation of transgenic individual plants of the two recipient varieties. The transgenic individual plants all showed the expected phenotype changes, that was, phenotype differences similar to those of near isogenic lines (FIG. 5a and FIG. 5b) and markedly higher phenotype values in number of spikelets per panicle, heading date and plant height as compared to controls (FIG. 5c and FIG. 5d). The T1 generation exhibited similar trait changes (Table 4) and showed the segregation ratio of a single gene, indicating that these transgenic individual plants contained a single copy of Ghd7 gene (Table 5) and that this gene can be used to modify rice varieties through genetic transformation.

TABLE 3

Primers of the present invention used in the separation of Ghd7 gene

| Name of primer | Forward primer (5'-3') | Reverse primer (5'-3') | Product size bp | Annealing temperature ° C. | Use |
| --- | --- | --- | --- | --- | --- |
| Cexu1-2 | gcaagggatgtctaaacga | aattttgaccgtcggattc | 950 | 55 | BAC clone screening |
| Cexu7-8 | catacggatccagcctctgt | ttgcaatgatgcgtattcac | 950 | 55 | BAC clone screening |
| Cexu13-14 | atttgtgccatgagagagca | ccccaaatatctttgccact | 950 | 55 | BAC clone screening |
| Full-cDNA | caacttgccctgtcttcttcttc | gatcagtcatatatagttagtg | 1014 | 50 | Full-length cDNA separation |

TABLE 4

Phenotypes of the T1 individual plants transformed with Ghd7 gene cloned in the present invention

| Genotype | Number of individual plants examined | Days from seeding to flowering | Plant height (cm) | Number of spikelets on main panicle |
| --- | --- | --- | --- | --- |
| Mudanjiang 8 | 10 | 53.0 ± 1.4 | 67.9 ± 1.1 | 69.3 ± 4.3 |
| Mudanjiang 8 (+) | 28 | 130.9 ± 1.5 | 106.8 ± 0.9 | 123.4 ± 3.8 |
| Mudanjiang 8 (−) | 11 | 59.8 ± 1.2 | 71.6 ± 1.3 | 65.0 ± 3.1 |
| | | P = 0.000000 | P = 0.000000 | P = 0.000000 |
| Hejiang 19 | 10 | 52.8 ± 0.7 | 60.7 ± 0.7 | 53.3 ± 3.9 |

TABLE 4-continued

Phenotypes of the T1 individual plants transformed with Ghd7 gene cloned in the present invention

| Genotype | Number of individual plants examined | Days from seeding to flowering | Plant height (cm) | Number of spikelets on main panicle |
|---|---|---|---|---|
| Hejiang 19 (+) | 25 | 104.3 ± 1.7 | 101.3 ± 1.2 | 161.7 ± 8.3 |
| Hejiang 19 (−) | 10 | 50.8 ± 1.5<br>P = 0.000000 | 60.7 ± 0.7<br>P = 0.000000 | 55.5 ± 2.1<br>P = 0.000000 |

Note:
(+) and (−) stand for positive and negative transgenic individual plants; P values represent the probability values of differences in traits between T1 generation positive and negative individual plants obtained by t-test.

TABLE 5

Segregation ratio test of the T1 generation transgenic for Ghd7

| Recipient | Number of individual plants with late heading, large ear and high stalk | Number of individual plants with early heading, small ear and short stalk | Chi-square value (3:1) |
|---|---|---|---|
| Moudanjian 8 | 36 | 11 | 0.0072 |
| Hejiang 19 | 25 | 10 | 0.085 |

Example 6

Gene Structure and Function Prediction of Ghd7

1) Gene Structure Analysis of Ghd7

After identification of function of the candidate gene using transgenic individual plants, the Ghd7 gene was determined to locate in the 8,175 bp region. Based on the sequence of Ghd7, primers 3' RACE (GTCATATTGTGGGAGCACGT; SEQ ID NO:12) and 5' RACE (ACCATCTCCT-TGGGCATCGA; SEQ ID NO:13) were designed. 5'- and 3'-terminal sequences were obtained using 5' and 3' RACE technology and full-length cDNA was therefore isolated. A 1,014 bp long cDNA was obtained, whose nucleotide sequence was as shown in SEQ ID NO: 2. The cDNA sequence of the cloned Ghd7 gene of the present invention matched well with the region from 1,469 bp to 3,884 in this 8,175 bp region. By comparing the sequence of the full-length cDNA with the 8,175 bp genomic sequence of Minghui 63, the structure of Ghd7 gene was obtained as follows: Ghd7 gene was 2,659 bp in length from the transcription start codon to the termination codon, comprising 2 exons and 1 intron; the starting exon was 444 bp in length, the second exon was 327 bp in length, and the intron was 1,647 bp in length (FIG. 6). Therefore, the open reading frame of Ghd7 gene was 771 bp in length and encodes 257 amino acids. The sequence of Ghd7 gene was as shown in SEQ ID NO: 1.

(2) Function Prediction of Ghd7

The protein structure comprising 277 amino acids encoded by Ghd7 gene was subjected to search by BLASTp. It was found that the region from the 189$^{th}$ amino acid to the 233$^{rd}$ amino acid comprises one gene having significant identity with the conserved CCT domain of the CO protein in *Arabidopsis* (74%, 2e-09) (Putterill et al. 1995) and also having high homology to many proteins associated with the regulation of plant flowering, such as flowering time control during light period (Putterill et al. 1995, Yano et al. 2000, Turner et al. 2005), spring flowering of wheat (Yan et al. 2004), biological clock (Strayer et al. 2000; Salome et al. 2006) and light signal (Kaczorowski and Quail 2003). However, Ghd7 has no distinct B-box zinc finger protein, therefore Ghd7 is a new member in the gene family having CCT domain.

Example 7

Determination of Base Pair Variation Between Ghd7 Alleles by Sequence Alignment

1. Sequencing

Four large ear varieties (Minghui 63, Teqing, 93-11 and HR5), two small ear varieties (Mudanjiang 8 and Hejiang 19) and two varieties with intermediate phenotypes (Zhonghua 11 and Nipponbare) were sequenced in the target region. Products covering the 8,175 bp were amplified using 3 pairs of PCR primers and the products were sequenced using 15 primers (Table 6). PCR amplification was carried out from the genome of these varieties using high fidelity LA-Taq (TakaRa Co., Japan). Then the PCR products were ligated into pGEM-T vector using pGEM-T Vector System 1 kit (Promega Co., USA) according to the manufacturer's specification and were transformed into *E. coli* DH10B (Invitrogen Co., USA). Positive clones were obtained by blue/white screening and sequencing was carried out from both ends of each subclone using T7-R and SP6-F universal primers (Shanghai Sangon Biological Engineering Technology and Services Co., Ltd., China) and Big Dye Kit (Perkin Elmer Co., USA). Sequence contigs were assembled using SEQUENCHER 4.1 software (Gene Codes Corporation, USA).

TABLE 6

Self-designed primers used for sequence alignment of the present invention

| Name of primer | Forward primer (5'-3') | Reverse primer (5'-3') | Product size* | Annealing temperature | Use |
|---|---|---|---|---|---|
| Full-cDNA | caacttgccctgtcttcttcttc | gatcagtcatatatagttagtg | 2659 | 50 | Full-length gene amplification |
| CEXU1-2 | gcaaggggatgtctaaacga | Aatttttgaccgtcggattc | 950 | 55 | Promoter region amplification |

TABLE 6-continued

Self-designed primers used for sequence alignment of the present invention

| Name of primer | Forward primer (5'-3') | Reverse primer (5'-3') | Product size* | Annealing temperature | Use |
|---|---|---|---|---|---|
| CEXU3-4 | ttgccgaagaactggaactc | ttgccgaagaactggaactc | 950 | 55 | Promoter region amplification |
| XUECEXU5-6 | ttatccgttcatgtcgatgg | accgaactcgaaaagcacac | | | Internal sequencing primer |
| XUECEXU7-8 | catacggatccagcctctgt | Ttgcaatgatgcgtattcac | | | Internal sequencing primer |
| CEXU3374 | tagaactgcaaggagatgca | | | | Internal sequencing primer |
| Cexue800 | | ctcttcttcctcttctccttg | | | Internal sequencing primer |
| CEXU4147 | gtcatattgtgggagcacgt | gaacggaacagaagttagct | 1870 | 50 | 3'-external region amplification |
| cexu4933 | caaagttccacgtatcctct | | | | Internal sequencing primer |
| CEXU6105 | | gtcgctggtgccaattatga | | | Internal sequencing primer |
| CEXU13-14 | atttgtgccatgagagagca | ccccaaatatctttgccact | 950 | 55 | 3'-external region amplification |

*The sizes of PCR products were determined according to the sequence of Nipponbare and they might vary depending on varieties.

2. Sequence Alignment

Figure 7:
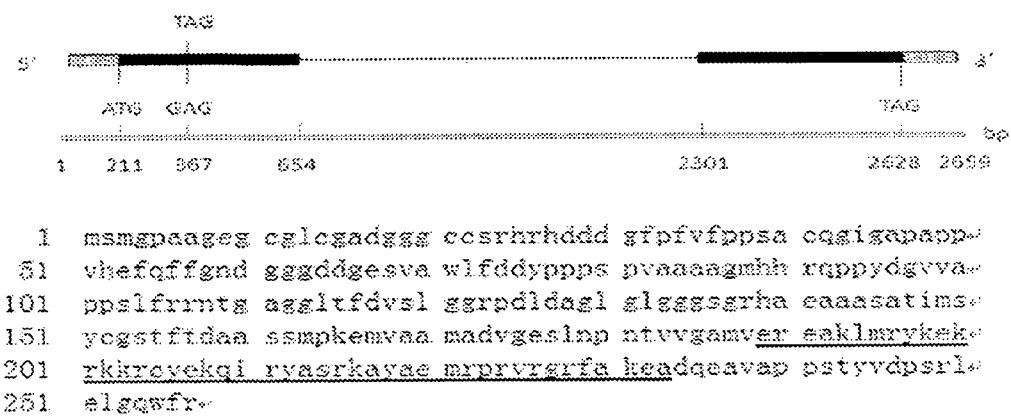
FIG. 7 is the structural diagram of the Ghd7 gene cloned in the present invention. The black boxes represent exons, and the boxes with slanted lines represent 5' and 3' UTR. "ATG" and "TGA" are translation start codon and stop codon respectively. The difference in one base between the large ear variety and the small ear variety is located in the first exon of Ghd7 gene, which a mutation from glutamic acid (GAG) in the small ear variety to the stop codon (TGA) in the large ear variety. The underlined interval is the CCT conserved domain. The polypeptide sequence shown is SEQ ID NO:32.

Sequence alignment in the target region was performed among four large ear varieties (Minghui 63, HR5, Teqing and 93-11) and two small ear varieties (Hejiang 19 and Mudanjiang 8). The information of Ghd7 region sequence of 93-11 came from contig AAAA02021502.1 (information available at the NCBI website). Sequence alignment was performed on Vector NTI9 software (InforMax™ Co., USA). Sequence analysis found that large ear varieties all had a stop mutation at the 53$^{rd}$ amino acid in the first exon (see FIG. 7). It is likely that this early stop mutation is the key mutation that affects gene function.

Example 7

Response of Ghd7 to Light Period Regulation

Ghd7 near isogenic lines with Zhenshan 95 background were subjected to long-day and short-day treatment. It was found that, under long-day treatment, the individual plants of Ghd7 alleles of Minghui 63 had markedly later heading date, taller plant height, larger number of spikelets per panicle and higher yield as compared with the Zhenshan 94 allelotype (Ghd7 deficient type). However, under short-day treatment, there was no difference between the two genotypes of near isogenic lines (Table 7). Under long-day and short-day conditions, Minghui 63 and Zhenshan 97 (MM) were extremely significantly different in the three traits; while Zhenshan 97 and Zhenshan 97 (ZZ) were significantly different in number of spikelets per panicle and were not significantly different in plant height and heading date. Obviously, Ghd7 delayed heading date under long-day condition.

TABLE 7

Phenotypes of two Ghd7 homozygous genotypes of near isogenic lines under long-day and short-day conditions

| Traits | Treatment | Zhenshan 97 | Zhenshan 97 (ZZ) | Minghui 63 | Zhenshan 97 (MM) |
|---|---|---|---|---|---|
| Heading date (Day) | Long-day | 62.5 ± 1.1 | 63.8 ± 1.0 | 90.3 ± 1.9 | 90.8 ± 2.2 |
| | Short-day | 63.1 ± 1.3 | 64.8 ± 2.2 | 75.3 ± 1.8 | 68.1 ± 2.7 |
| | Difference | −0.6 | −1.0 | 15.0 ** | 22.7 ** |
| Plant height (cm) | Long-day | 78.2 ± 2.3 | 74.3 ± 3.6 | 102.4 ± 2.7 | 105.3 ± 5.1 |
| | Short-day | 75.3 | 71.3 ± 3.1 | 86.7 ± 2.1 | 80.5 ± 4.1 |
| | Difference | 2.9 | 3.0 | 15.7 ** | 24.8 ** |
| Number of spikelets per panicle | Long-day | 88.7 ± 4.4 | 86.7 ± 5.3 | 155.4 ± 7.8 | 152.6 ± 5.7 |
| | Short-day | 80.4 ± 5.3 | 78.5 ± 5.0 | 96.1 ± 4.8 | 84.9 ± 7.0 |
| | Difference | 8.3 * | 8.2 * | 59.3 ** | 67.7 ** |

Zhenshan 97 (ZZ) and Zhenshan 97 (MM) represent near isogenic lines with Zhenshan 97 background, respectively;
* and ** represent significant difference at 5% and 1% level, respectively.

We claim:

1. A transformed plant comprising a recombinant DNA construct comprising a promoter functional in a plant cell positioned to provide for expression of a polynucleotide that comprises the coding region of the nucleotide sequence of SEQ ID NO: 1.

2. A transformed plant comprising a recombinant DNA construct comprising a promoter functional in a plant cell positioned to provide for expression of a polynucleotide encoding a polypeptide that comprises the polypeptide sequence of SEQ ID NO:32.

3. The transformed plant according to claim 1, wherein said plant is a crop plant.

4. The transformed plant according to claim 1, wherein said transgenic plant has an altered trait as compared to a non-transformed plant or wild-type plant, wherein said altered trait is selected from the group consisting of delayed heading date, increased plant height, increased number of spikelets per panicle, and increased yield.

5. The transformed plant according to claim 4, wherein said plant is a crop plant.

6. A method of producing a transformed plant having an altered trait, wherein said method comprises transforming a plant cell with a recombinant construct comprising a promoter functional in a plant cell positioned to provide for expression of a polynucleotide that comprises the coding region of the nucleotide sequence of SEQ ID NO: 1 and obtaining from said cell a transformed plant that shows delayed heading date, increased plant height, increased numbers of spikelets per panicle and increased yield as compared to a non-transformed plant or wild-type plant.

7. A method of producing a transformed plant having an altered trait, wherein said method comprises transforming a plant with a recombinant construct comprising a promoter functional in a plant cell positioned to provide for expression of a polynucleotide encoding a polypeptide that comprises the polypeptide sequence of SEQ ID NO: 32 and obtaining a transformed plant that shows delayed heading date, increased plant height, increased numbers of spikelets per panicle and increased yield as compared to a non-transformed plant or wild-type plant.

8. The method according to claim 6 or 7, wherein said transformed plant is a crop plant.

* * * * *

SEQUENCE LISTING

<160> NUMBER OF SEQ ID NOS: 32

<210> SEQ ID NO 1
<211> LENGTH: 3917
<212> TYPE: DNA
<213> ORGANISM: Oryza sativa
<220> FEATURE:
<221> NAME/KEY: gene
<222> LOCATION: (1)..(3917)
<220> FEATURE:
<221> NAME/KEY: 5'UTR
<222> LOCATION: (1259)..(1468)
<220> FEATURE:
<221> NAME/KEY: CDS
<222> LOCATION: (1469)..(1912)
<220> FEATURE:
<221> NAME/KEY: exon
<222> LOCATION: (1469)..(1912)
<220> FEATURE:
<221> NAME/KEY: Intron
<222> LOCATION: (1913)..(3557)
<220> FEATURE:
<221> NAME/KEY: CDS
<222> LOCATION: (3558)..(3884)
<220> FEATURE:
<221> NAME/KEY: exon
<222> LOCATION: (3558)..(3884)
<220> FEATURE:
<221> NAME/KEY: 3'UTR
<222> LOCATION: (3885)..(3917)

<400> SEQUENCE: 1

```
gagggatgag acggcacgac aacgccctca tgagggggaa tgaatcatcg ttgtcggtac      60
ggtcaaaacc aggctgggtt ttcacccacc gctcatcacc tgcaaatcta cggctgacgc     120
accgatgctc caccacagct caacctctgc cgatgtgtgg gaccactgca ccccctcccc     180
gccggctagc cttcgtacgc cgaagactgc gccacaccct caatctatta tcagtcatat     240
gtatgagagc aaccacggta tatcgaaagg taaccttatg gcaataatta catttataaa     300
gtggaacaca tacattgtga gaaatagctt tagcttagag tgcatcttat acttaaggtc     360
tacgacaagc aaaaagaaaa tattctctct cttatttatg tcatgaacaa gagctgaaaa     420
gcaggttttt ctatctcata tgggccccat attattgtta aatttcagca agggattagc     480
taaaaaactg ttgcaggttt tttgagtaaa aaactttcaa atctaactat agtatataat     540
tttactagaa ctacattata acaattatat aacttgtata gatgtattaa ataatatat      600
gcaactttat atctaatttg atagagataa taatgtagtt actgtaacta gggtataact     660
gaagtataac taacatgtaa cttgctaatt ttttaaaaaa cttgcaagct ggtgggatcg     720
aggtcctggg ttcgaacccc atgcagcgca caaattatgt ttctcacacg ggatttttt      780
ccatgaacgc gccagcacga atcttgagat gaatccgacg gtcaaaaatt cgaagaatt      840
tacccctgtt ttctgtccat agaaaactag caaatctgtt tcagcaatag cattatgaga     900
attgctttaa caacaatcaa actattcatg gccgcttct aagatcacac tagactcata      960
tacattgaga ttgccctgat atatccatct aattcatgga cattttccta gtcttggggg    1020
gatatagtat aataggagct agagggggggc atgggtagtg aagtccagcc agcacagaag    1080
atccttgggg ggatctggtt gcaatgggga tggccaatga ggagtcgcca aattatcagg    1140
tgaaaaaagg cggccggatt cctccacgta aggaccaaat ccatccacag atcgccccgc    1200
tctcctcgat cgatcataat atgatctcgc aatggccccc ctacctttcc ctcatcccca    1260
acttgccctg tcttcttctt cttcttcttc ttgtacctat attattacaa gtcatcgatc    1320
```

```
                                                         -continued tcgctgatcg atcagtgatc acaagcattt cacaacccta gctagctgag ctgatcgagc        1380
tcaagtgacc tcacctgcta tagctaactt actagctagc tctagctagt tgttgtttgt        1440
agctcgatcg agtttgattt atccgttc atg tcg atg gga cca gca gcc gga          1492
                                Met Ser Met Gly Pro Ala Ala Gly
                                 1               5 gaa gga tgt ggc ctg tgc ggc gcc gac ggt ggc tgt tgc tcc cgc              1540
Glu Gly Cys Gly Leu Cys Gly Ala Asp Gly Gly Cys Cys Ser Arg
    10              15                  20 cat cgc cac gat gat gat gga ttc ccc ttc gtc ttc ccg ccg agt gcg          1588
His Arg His Asp Asp Asp Gly Phe Pro Phe Val Phe Pro Pro Ser Ala
25              30                  35                  40 tgc cag ggg atc ggc gcc ccg gcg cca ccg gtg cac gag ttc cag ttc          1636
Cys Gln Gly Ile Gly Ala Pro Ala Pro Pro Val His Glu Phe Gln Phe
                45                  50                  55 ttc ggc aac gac ggc ggc ggc gac gac ggc gag agc gtg gcc tgg ctg          1684
Phe Gly Asn Asp Gly Gly Gly Asp Asp Gly Glu Ser Val Ala Trp Leu
            60                  65                  70 ttc gat gac tac ccg ccg ccg tcg ccc gtt gct gcc gcc gcc ggg atg          1732
Phe Asp Asp Tyr Pro Pro Pro Ser Pro Val Ala Ala Ala Ala Gly Met
        75                  80                  85 cat cat cgg cag ccg ccg tac gac ggc gtc gtg gcg ccg ccg tcg ctg          1780
His His Arg Gln Pro Pro Tyr Asp Gly Val Val Ala Pro Pro Ser Leu
    90                  95                  100 ttc agg agg aac acc ggc gcc ggc ggg ctc acg ttc gac gtc tcc ctc          1828
Phe Arg Arg Asn Thr Gly Ala Gly Gly Leu Thr Phe Asp Val Ser Leu
105                 110                 115                 120 ggc gga cgg ccc gac ctg gac gcc ggg ctc ggc ctc ggc ggc ggc agc          1876
Gly Gly Arg Pro Asp Leu Asp Ala Gly Leu Gly Leu Gly Gly Gly Ser
                125                 130                 135 ggc cgg cac gcc gag gcc gcg gcc agc gcc acc atc gtgagtatca              1922
Gly Arg His Ala Glu Ala Ala Ala Ser Ala Thr Ile
            140                 145 atccaataat cctgatccgg ccggcatgat cggctcgatc gagccgtgtc gattattaat        1982
ttccatctta tatattatta attgatgaat tcttgattga ttcatcgatc ctcctcgtct        2042
tttcttggct tccttgtttt tgttatttag tcaaaaacaa ctcttcattt ctgctgccta        2102
tatgccgtac aacttcaaac tatcaaaggt caaataatcg atcaatatat accaagtttg        2162
aattaatttg gagcttaatt aattaattac tggcttgcag cagctggttt atagtattgt        2222
ttctagctat atatgtgagg gccgtgtgtg ggatgtgatt tgcatctttc gatggcgact        2282
taattaattc gatgatatat ttcattgcat atgcatacgg atccagcctc tgtctatact        2342
gtacgattcc acatacgtat atgtacggtt aagtcagtat atatactttt agatagtcgc        2402
gtgtgctttt cgagttcggt agctatattt tagattgtaa aaacaagtca gaggctaatt        2462
ttataatcta gaaatactta tttccccgta taaccgta tgttaaatat tgatggtgta         2522
atctacttat aagtcaggaa acatcattgc ttgctttctg gcgctttctt ctacatatca        2582
gtagaggaaa atggaaaaaa aaaagatgaa ttttgatgtt gtagtttgct atattcagca        2642
tatatgccat cagttataca tatgcagatc ttgctaaaac caaaataaaa atagaactgt        2702
aaggagatat tgtgcttctc ggtctattta cttacagttt gttgagaagt aatacgagca        2762
agcaaatgta tatatatatt tctttagaac tgcaaggaga tgcatataca tgtgtgattc        2822
aaacacacgt actgcacatt caaactataa aaacaacttg attgccgtag aagttaaaag        2882
ggagacatat ccatgggttt cggattctaa atcaatctat gtgtaaatga aacttttagta      2942 tagtaggaaa taggttttca aaaaaaaagt atagtaggaa atagtatgtg tatatgcctt        3002
```

```
tttaacccctt aattacaagt tgtaataatt cagtgttaac aaagtcacgg actcacagag      3062 tgtgcccctta cacaatttca gactaatttg taaatgcatc gatcgtcaca ttttatgtgg     3122
ttcaattatc tgacacagtt aattaatggt ggccgatcga tgtatgctcc tctagctttc      3182
cagctatatg cgtatgtaat aaatgaataa aacgtgtagg atgaaatgtg aatacgcatc     3242
attgcaatta atttgattaa tgctagtaaa aaatctgcaa atttgtcttt tgaaattaa      3302 aatatgcctt ataaaattaa tggacccagg cccctaggcc aaaatatatt ggggcacaaa     3362
atcatgtcca tatatacatt cttatttgaa agtagactct gaaacaaaat atgcccatat    3422
aaatcaaggg aggttacaac taactgcatt tgcttatgcg tacatctgga ttgtaacttc    3482
tacgttttgt acatacgatg attaattgta ttcgagcttc ttaattgtac atctattaac    3542
taactagttt tgcag atg tca tat tgt ggg agc acg ttc act gac gca gcg    3593
                  Met Ser Tyr Cys Gly Ser Thr Phe Thr Asp Ala Ala
                      150              155                 160 agc tcg atg ccc aag gag atg gtg gcc gcc atg gcc gat gtt ggg gag     3641
Ser Ser Met Pro Lys Glu Met Val Ala Ala Met Ala Asp Val Gly Glu
            165                 170                 175 agc ttg aac cca aac acg gtg gtt ggc gca atg gtg gag agg gag gcc     3689
Ser Leu Asn Pro Asn Thr Val Val Gly Ala Met Val Glu Arg Glu Ala
        180                 185                 190 aag ctg atg agg tac aag gag aag agg aag aag agg tgc tac gag aag     3737
Lys Leu Met Arg Tyr Lys Glu Lys Arg Lys Lys Arg Cys Tyr Glu Lys
    195                 200                 205 caa atc cgg tac gcg tcc aga aaa gcc tat gcc gag atg agg ccc cga     3785
Gln Ile Arg Tyr Ala Ser Arg Lys Ala Tyr Ala Glu Met Arg Pro Arg
210                 215                 220 gtg aga ggt cgc ttc gcc aaa gaa gct gat cag gaa gct gtc gca ccg     3833
Val Arg Gly Arg Phe Ala Lys Glu Ala Asp Gln Glu Ala Val Ala Pro
225                 230                 235                 240 cca tcc acc tat gtc gat cct agt agg ctt gag ctt gga caa tgg ttc     3881
Pro Ser Thr Tyr Val Asp Pro Ser Arg Leu Glu Leu Gly Gln Trp Phe
                245                 250                 255 aga tagataatta cagtgcgtat ataccactaa cta                             3917
Arg

<210> SEQ ID NO 2
<211> LENGTH: 148
<212> TYPE: PRT
<213> ORGANISM: Oryza sativa

<400> SEQUENCE: 2

Met Ser Met Gly Pro Ala Ala Gly Glu Gly Cys Gly Leu Cys Gly Ala
1               5                   10                  15

Asp Gly Gly Cys Cys Ser Arg His Arg His Asp Asp Gly Phe
            20                  25                  30

Pro Phe Val Phe Pro Pro Ser Ala Cys Gln Gly Ile Gly Ala Pro Ala
            35                  40                  45

Pro Pro Val His Glu Phe Gln Phe Gly Asn Asp Gly Gly Gly Asp
        50                  55                  60

Asp Gly Glu Ser Val Ala Trp Leu Phe Asp Asp Tyr Pro Pro Ser
65                  70                  75                  80

Pro Val Ala Ala Ala Gly Met His His Arg Gln Pro Pro Tyr Asp
                85                  90                  95

Gly Val Val Ala Pro Pro Ser Leu Phe Arg Arg Asn Thr Gly Ala Gly
            100                 105                 110

Gly Leu Thr Phe Asp Val Ser Leu Gly Gly Arg Pro Asp Leu Asp Ala
        115                 120                 125
```

Gly Leu Gly Leu Gly Gly Gly Ser Gly Arg His Ala Glu Ala Ala Ala
            130                 135                 140

Ser Ala Thr Ile
145

<210> SEQ ID NO 3
<211> LENGTH: 109
<212> TYPE: PRT
<213> ORGANISM: Oryza sativa

<400> SEQUENCE: 3

Met Ser Tyr Cys Gly Ser Thr Phe Thr Asp Ala Ala Ser Ser Met Pro
1               5                   10                  15

Lys Glu Met Val Ala Ala Met Ala Asp Val Gly Glu Ser Leu Asn Pro
            20                  25                  30

Asn Thr Val Val Gly Ala Met Val Glu Arg Glu Ala Lys Leu Met Arg
        35                  40                  45

Tyr Lys Glu Lys Arg Lys Lys Arg Cys Tyr Glu Lys Gln Ile Arg Tyr
    50                  55                  60

Ala Ser Arg Lys Ala Tyr Ala Glu Met Arg Pro Arg Val Arg Gly Arg
65                  70                  75                  80

Phe Ala Lys Glu Ala Asp Gln Glu Ala Val Ala Pro Pro Ser Thr Tyr
                85                  90                  95

Val Asp Pro Ser Arg Leu Glu Leu Gly Gln Trp Phe Arg
            100                 105

<210> SEQ ID NO 4
<211> LENGTH: 20
<212> TYPE: DNA
<213> ORGANISM: Oryza sativa

<400> SEQUENCE: 4
gcaaggggat gtctaaacga                                              20

<210> SEQ ID NO 5
<211> LENGTH: 20
<212> TYPE: DNA
<213> ORGANISM: Oryza sativa

<400> SEQUENCE: 5
aatttttgac cgtcggattc                                              20

<210> SEQ ID NO 6
<211> LENGTH: 20
<212> TYPE: DNA
<213> ORGANISM: Oryza sativa

<400> SEQUENCE: 6
catacggatc cagcctctgt                                              20

<210> SEQ ID NO 7
<211> LENGTH: 20
<212> TYPE: DNA
<213> ORGANISM: Oryza sativa

<400> SEQUENCE: 7
ttgcaatgat gcgtattcac                                              20

<210> SEQ ID NO 8
<211> LENGTH: 20
<212> TYPE: DNA

<213> ORGANISM: Oryza sativa

<400> SEQUENCE: 8
atttgtgcca tgagagagca                    20

<210> SEQ ID NO 9
<211> LENGTH: 20
<212> TYPE: DNA
<213> ORGANISM: Oryza sativa

<400> SEQUENCE: 9
ccccaaatat ctttgccact                    20

<210> SEQ ID NO 10
<211> LENGTH: 23
<212> TYPE: DNA
<213> ORGANISM: Oryza sativa

<400> SEQUENCE: 10
caacttgccc tgtcttcttc ttc                23

<210> SEQ ID NO 11
<211> LENGTH: 22
<212> TYPE: DNA
<213> ORGANISM: Oryza sativa

<400> SEQUENCE: 11
gatcagtcat atatagttag tg                 22

<210> SEQ ID NO 12
<211> LENGTH: 20
<212> TYPE: DNA
<213> ORGANISM: Oryza sativa

<400> SEQUENCE: 12
gtcatattgt gggagcacgt                    20

<210> SEQ ID NO 13
<211> LENGTH: 20
<212> TYPE: DNA
<213> ORGANISM: Oryza sativa

<400> SEQUENCE: 13
accatctcct tgggcatcga                    20

<210> SEQ ID NO 14
<211> LENGTH: 23
<212> TYPE: DNA
<213> ORGANISM: Oryza sativa

<400> SEQUENCE: 14
caacttgccc tgtcttcttc ttc                23

<210> SEQ ID NO 15
<211> LENGTH: 22
<212> TYPE: DNA
<213> ORGANISM: Oryza sativa

<400> SEQUENCE: 15
gatcagtcat atatagttag tg                 22

<210> SEQ ID NO 16
<211> LENGTH: 20
<212> TYPE: DNA

-continued

<213> ORGANISM: Oryza sativa

<400> SEQUENCE: 16
gcaaggggat gtctaaacga                                              20

<210> SEQ ID NO 17
<211> LENGTH: 20
<212> TYPE: DNA
<213> ORGANISM: Oryza sativa

<400> SEQUENCE: 17
aatttttgac cgtcggattc                                              20

<210> SEQ ID NO 18
<211> LENGTH: 20
<212> TYPE: DNA
<213> ORGANISM: Oryza sativa

<400> SEQUENCE: 18
ttgccgaaga actggaactc                                              20

<210> SEQ ID NO 19
<211> LENGTH: 20
<212> TYPE: DNA
<213> ORGANISM: Oryza sativa

<400> SEQUENCE: 19
ttgccgaaga actggaactc                                              20

<210> SEQ ID NO 20
<211> LENGTH: 20
<212> TYPE: DNA
<213> ORGANISM: Oryza sativa

<400> SEQUENCE: 20
ttatccgttc atgtcgatgg                                              20

<210> SEQ ID NO 21
<211> LENGTH: 20
<212> TYPE: DNA
<213> ORGANISM: Oryza sativa

<400> SEQUENCE: 21
accgaactcg aaaagcacac                                              20

<210> SEQ ID NO 22
<211> LENGTH: 20
<212> TYPE: DNA
<213> ORGANISM: Oryza sativa

<400> SEQUENCE: 22
catacggatc cagcctctgt                                              20

<210> SEQ ID NO 23
<211> LENGTH: 20
<212> TYPE: DNA
<213> ORGANISM: Oryza sativa

<400> SEQUENCE: 23
ttgcaatgat gcgtattcac                                              20

<210> SEQ ID NO 24
<211> LENGTH: 20
<212> TYPE: DNA

<213> ORGANISM: Oryza sativa

<400> SEQUENCE: 24
tagaactgca aggagatgca                                          20

<210> SEQ ID NO 25
<211> LENGTH: 21
<212> TYPE: DNA
<213> ORGANISM: Oryza sativa

<400> SEQUENCE: 25
ctcttcttcc tcttctcctt g                                        21

<210> SEQ ID NO 26
<211> LENGTH: 20
<212> TYPE: DNA
<213> ORGANISM: Oryza sativa

<400> SEQUENCE: 26
gtcatattgt gggagcacgt                                          20

<210> SEQ ID NO 27
<211> LENGTH: 20
<212> TYPE: DNA
<213> ORGANISM: Oryza sativa

<400> SEQUENCE: 27
gaacggaaca gaagttagct                                          20

<210> SEQ ID NO 28
<211> LENGTH: 20
<212> TYPE: DNA
<213> ORGANISM: Oryza sativa

<400> SEQUENCE: 28
caaagttcca cgtatcctct                                          20

<210> SEQ ID NO 29
<211> LENGTH: 20
<212> TYPE: DNA
<213> ORGANISM: Oryza sativa

<400> SEQUENCE: 29
gtcgctggtg ccaattatga                                          20

<210> SEQ ID NO 30
<211> LENGTH: 20
<212> TYPE: DNA
<213> ORGANISM: Oryza sativa

<400> SEQUENCE: 30
atttgtgcca tgagagagca                                          20

<210> SEQ ID NO 31
<211> LENGTH: 20
<212> TYPE: DNA
<213> ORGANISM: Oryza sativa

<400> SEQUENCE: 31
ccccaaatat ctttgccact                                          20

<210> SEQ ID NO 32
<211> LENGTH: 257
<212> TYPE: PRT

-continued

```
<213> ORGANISM: Oryza sativa

<400> SEQUENCE: 32

Met Ser Met Gly Pro Ala Ala Gly Glu Gly Cys Gly Leu Cys Gly Ala
1               5                   10                  15

Asp Gly Gly Gly Cys Cys Ser Arg His Arg His Asp Asp Asp Gly Phe
            20                  25                  30

Pro Phe Val Phe Pro Pro Ser Ala Cys Gln Gly Ile Gly Ala Pro Ala
        35                  40                  45

Pro Pro Val His Glu Phe Gln Phe Phe Gly Asn Asp Gly Gly Gly Asp
    50                  55                  60

Asp Gly Glu Ser Val Ala Trp Leu Phe Asp Asp Tyr Pro Pro Pro Ser
65                  70                  75                  80

Pro Val Ala Ala Ala Ala Gly Met His His Arg Gln Pro Pro Tyr Asp
                85                  90                  95

Gly Val Val Ala Pro Pro Ser Leu Phe Arg Arg Asn Thr Gly Ala Gly
            100                 105                 110

Gly Leu Thr Phe Asp Val Ser Leu Gly Gly Arg Pro Asp Leu Asp Ala
            115                 120                 125

Gly Leu Gly Leu Gly Gly Gly Ser Gly Arg His Ala Glu Ala Ala Ala
            130                 135                 140

Ser Ala Thr Ile Met Ser Tyr Cys Gly Ser Thr Phe Thr Asp Ala Ala
145                 150                 155                 160

Ser Ser Met Pro Lys Glu Met Val Ala Met Ala Asp Val Gly Glu
                165                 170                 175

Ser Leu Asn Pro Asn Thr Val Val Gly Ala Met Val Glu Arg Glu Ala
            180                 185                 190

Lys Leu Met Arg Tyr Lys Glu Lys Arg Lys Lys Arg Cys Tyr Glu Lys
            195                 200                 205

Gln Ile Arg Tyr Ala Ser Arg Lys Ala Tyr Ala Glu Met Arg Pro Arg
        210                 215                 220

Val Arg Gly Arg Phe Ala Lys Glu Ala Asp Gln Glu Ala Val Ala Pro
225                 230                 235                 240

Pro Ser Thr Tyr Val Asp Pro Ser Arg Leu Glu Leu Gly Gln Trp Phe
                245                 250                 255

Arg
```